(12) United States Patent
Dahmen et al.

(10) Patent No.: US 6,403,700 B1
(45) Date of Patent: *Jun. 11, 2002

(54) ABSORBING AGENTS FOR WATER AND AQUEOUS LIQUIDS AND PROCESS FOR THEIR PRODUCTION AND USE

(75) Inventors: Kurt Dahmen, Mönchengladbach; Reinmar Peppmöller, Krefeld, both of (DE)

(73) Assignee: Stockhausen GmbH & Co. KG, Krefeld (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/532,085

(22) Filed: Mar. 21, 2000

Related U.S. Application Data

(63) Continuation of application No. 09/000,497, filed as application No. PCT/EP96/03203 on Jul. 19, 1996, now Pat. No. 6,060,557.

(30) Foreign Application Priority Data

Aug. 9, 1995 (DE) .......................................... 195 29 348

(51) Int. Cl.$^7$ .............................. C08J 3/00; C08K 3/20; C08L 31/00; C08L 33/00; C08F 8/00
(52) U.S. Cl. ................... 524/556; 174/118; 174/110 V; 385/115; 525/119; 525/326.3; 525/329.7; 525/330.2
(58) Field of Search .......................... 524/556; 525/119, 525/326.3, 329.7, 330.2; 604/358, 372; 174/118, 110 V; 385/115

(56) References Cited

U.S. PATENT DOCUMENTS 5,712,316 A * 1/1998 Dahmen et al.
6,060,557 A * 5/2000 Dahmen et al. ............ 524/556

FOREIGN PATENT DOCUMENTS

WO        WO95/02002        * 1/1995

* cited by examiner

*Primary Examiner*—Patrick D. Niland
(74) *Attorney, Agent, or Firm*—Oblon, Spivak, McClelland, Maier & Neustadt, P.C.

(57) ABSTRACT

The present invention relates to a powdery, cross-linked polymer absorbing water and aqueous liquids formed of polymerized, unsaturated, acid groups-containing monomers that are present as salts neutralized to the extent of at least 50 mol-% and which optionally comprise further monomers which are copolymerizable with the acid groups-containing monomers as well as water-soluble polymers, the polymer being formed of acidic, polymerized monomers partially neutralized to the extent of 5–30 mol-%, relative to the acid groups-containing monomer portion. The polymer has a high retention, high liquid absorption under pressure, high swelling pressure, and a low content of soluble components. The present invention further relates to a process for the production of said polymer and to its use as a component in sanitary articles which absorb body fluids and in wound dressings, in current-conducting and light-transmitting cables, as soil conditioners, as a component in packaging materials and in depot materials for the controlled release of active substances.

7 Claims, No Drawings

ABSORBING AGENTS FOR WATER AND AQUEOUS LIQUIDS AND PROCESS FOR THEIR PRODUCTION AND USE

This application is a Continuation of application Ser. No. 09/000,497 Filed on Apr. 23, 1998 now U.S. Pat. No. 6,060,557 which was originally filed as International Application No. PCT/EP96/03203, filed Jul. 19, 1996.

The present invention relates to water-insoluble, water-swellable polymers having a high absorption capacity for water and aqueous liquids, which are based on cross-linked, hydrophilic homopolymers and copolymers, as well as on graft polymers of ethylenically unsaturated, acid groups-containing, polymerizable monomers. The present invention further relates to the production method and the use of these polymers Polymers absorbing large amounts of aqueous liquids, in particular body fluids such as urine, are known as superabsorbent polymers.

The absorbent s are produced by radical polymerization under preferred use of monoethylenically unsaturated carboxylic acids, such as acrylic acid and its alkali salts, in aqueous solution, or according to the methods of inverse suspension or emulsion polymerization which are described in U.S. Pat. No. 4,286,082, DE 27 06 135, U.S. Pat. No. 4,340,706, DE 37 13 601, and DE 2840 010.

Polymers having different absorption properties can produced by selection of the monomer composition, cross-linkers, and polymerization conditions and processing conditions for the polymer gel. Additional possibilities are offered by the production of graft polymers, for example, by using chemically modified starch, cellulose, and polyvinyl alcohol according to DE 26 12 846, and by aftertreating the polymer gels or powdery resins by secondary surface cross-linkage of the polymer particles, for example, according to DE 40 20 780 C1.

For application of the polymers in hygienics and the sanitary field, polymers are produced whose neutralization degree ranges between 50 and 80 mol-%, relative to the polymerized, acid groups-containing monomer units, so that hydrogels are formed which have a skin neutral effect when used.

The degree of neutralization may be adjusted in different manners, neutralization or partial neutralization of the acidic monomers frequently being carried out prior to polymerization. However, neutralization or partial neutralization of a hydrogel comprising acidic, polymerized monomer units is also known.

According to EP205 674 A1 advantageously fully acidic polymers are produced at temperatures ranging from 0 to 100° C., preferably 5 to 40° C., which are adjusted by subsequent partial neutralization of the hydrogel. The polymers stand out for an improved gel strength and absorption capacity, as well as for a small portion of water-soluble polymers.

According to U.S. Pat. No. 5,145,906 and EP 530 438 B1 polymer gels of acrylic acid together with water-soluble, hydroxyl groups-containing polymers are produced at temperatures ranging from 5 to 20° C. under adiabatic conditions without neutralization of the monomers; subsequently the polymer gels are reduced in size and partially or completely neutralized by aqueous bases, comminuted again in the presence of a secondary cross-linking agent, and subjected to a heat treatment.

The mentioned methods are disadvantageous, because polymerization of the monomer solution, as is demonstrated in EP 467 073 A1, takes place very slowly so that it can only be carried out dis-continuously in a batch method. Increasing the amount of initiator or elevating the reaction temperature affects the desired polymer properties. Furthermore, it is difficult to comminute the entirely acidic polymer gel, and neutralization takes place slowly because of the procedure which is governed by diffusion. In this connection, excess base remains in the surface region of the polymer particles, while still reactive, polymerized, acid groups-containing monomer units are present in the gel interior where they are not available for subsequent cross-linkage in the surface region.

EP 467 073 A1 describes polymers which are obtained at a controlled polymerization temperature in the range of 20 to 70° C., in particular at 55 to 60° C., within 5 hours. According to the described method the polyacrylic acid is then neutralized to a degree of 72%. The dry and ground polymer is then subjected to the subsequent cross-linking process. However, if liquids are absorbed under pressure, the polymers obtained according to this process have an only limited liquid absorption capacity. Additionally, after liquid absorption, the known polymers have a substantial rewet behavior which is disadvantageous, in particular when they are used in hygienic articles.

Accordingly, there is the object to provide polymers with improved absorption properties, in particular with improved liquid absorption under pressure load and improved rewet behavior, and a process for their production under reduction of the polymerization period and improvement of the subsequent cross-linkage.

This object is achieved by a powdery, cross-linked polymer absorbing water and aqueous liquids which is formed of a) 55–99.9%-wt. of at least one polymerized, unsaturated, polymerizable, acid groups-containing monomer which is present as a salt neutralized to the extent of at least 50 mol-%, b) 0–40%-wt. of a polymerized, unsaturated monomer which is copolymerizable with the monomer according to a), c) 0.01–5.0%-wt. of at least one cross-linking agent, and d) 0–30%-wt. of a water-soluble polymer, with the sum of components a)–d) amounting to 100%-wt., which polymer is characterized by the fact that it is formed of acidic polymer gels partially neutralized to the extent of 5–30 mol-%, relative to the acid groups-containing monomer portion, and that it has a retention for a 0.9% aqueous NaCl-solution of at least 25 g/g polymer, a liquid absorption under a pressure of 50 g/cm$^2$ of at least 25 g/g polymer, a swelling pressure after 20 minutes of at least 700 g, relative to 1 g polymer, a maximum soluble content after 16 h of 10%-wt., preferably a maximum of 3%-wt., and a maximum rewet of 2.0 g.

The object is further achieved by a process for the production of this polymer, which is characterized by the fact that an aqueous solution having a maximum monomer content of 30% by weight, relative to the total solution, is produced; the unsaturated, polymerizable, acid groups-containing monomers are neutralized with bases to the extent of 5.0–30 mol-%, preferably 10–20 mol-%, prior to polymerization; the polymerization under radical conditions at a temperature ranging from 5–30° C., preferably 8–15° C., is initiated by chemical initiators and/or UV-irradiation and continued adiabatically; the polymer gel is subjected to a comminution after coarse grinding, and is neutralized with bases such that the polymer comprises a content of polymerized, neutralized, acid groups-containing monomer units of at least 50 mol-%; the polymer gel is dried to a water content of $\leq 10\%$-wt.; and that the dry and ground polymer is reacted at a temperature in the range of 140–240° C. with at least one bi- or multifunctional cross-linker reactive with acid groups.

Most surprisingly, we have found that polymers having a high retention value and high absorption capacity under a constant or increasing pressure, and low soluble polymer components are obtained, if the polymerization is carried out with a solution wherein a small amount of the acid groups-containing monomers have been neutralized by the addition of bases, instead of using a completely acid polymer solution. The range of partial neutralization amounts to about 5–30 mol-%, preferably 5–20 mol-%, and most preferably 5–10 mol-%, relative to acid groups-containing monomers.

According to the present invention water-soluble, monoethylenically unsaturated mono- and dicarboxylic acids, such as acrylic acid, methacrylic acid, ethacrylic acid, crotonic acid, sorbic acid, maleic acid, fumaric acid, itaconic acid, as well as vinylsulfonic acid; acrylamido- and/or methacrylamidoalkyl sulfonic acids, such as 2-acrylamido-2-methylpropane sulfonic acid, 2-methacryloyl oxyethane sulfonic acid, 4-vinylbenzene sulfonic acid, allyl sulfonic acid, vinyltoluene sulfonic acid, vinylphosphonic acid, and vinylbenzene phosphonic acid, are used as polymerizable, unsaturated, acid groups-containing monomers a).

Acrylic acid is the preferred water-soluble, unsaturated carboxylic acid. The proportion of other unsaturated carboxylic acids in the polymer, in addition to acrylic acid, may amount to up to 50%-wt.

Water-soluble, monoethylenically unsaturated monomers, such as acrylamide, methacrylamide, N-alkylated (meth) acrylamides, N-methylol (meth)acrylamide, N-vinyl amides, N-vinyl formamide, N-vinyl acetamide, and N-vinyl-N-methylacetamide, N-vinyl-N-methylformamide, vinylpyrrolidone, as well as hydroxyalkyl (meth)-acrylates, such as hydroxyethyl acrylate and (meth) acrylic acid esters of polyethylene glycol monoallyl ether, and allyl ethers of polyethylene glycols are used as monomers b).

Acrylic acid and methacrylic acid esters, such as ethyl acrylate and methyl acrylate, vinyl acetate and styrene are also used in limited amounts as monomers b) with a low solubility in water.

The maximum portion of these poorly or sparingly water-soluble monomers amounts to 10%-wt., relative to the sum of all monomers.

The mentioned monomers are used to produce homopolymers or copolymers with at least two monomers in any desired combination. The monomer mixture may additionally comprise a content of 0–30%-wt. of water-soluble polymers d), relative to the components of the monomer solution. A synthetic polymer or copolymer and/or a natural polymer and/or a derivative of a natural polymer may be used as water-soluble polymer. Examples thereof include water-soluble homo- and copolymers of the above-mentioned monomers, such as polyacrylic acid, partially saponified polyvinyl acetate, polyvinyl alcohol, polyalklyene glycol, starch, starch derivatives, graftpolymerized starch, cellulose and cellulose derivatives, such as carboxymethylcellulose, hydroxymethylcellulose, as well as galactomannan and its oxalkylated derivatives.

The aqueous monomer solution comprises at least one cross-linking agent c) in an amount of 0.01–5.0%-wt., preferably 0.1–2.0%-wt., relative to all portions of components a), b), and c) of the monomer solution. Any compound may be used as cross-linker which comprises at least two ethylenically unsaturated double-bonds, or one ethylenically unsaturated double-bond and one functional group reactive towards acid groups, or several functional groups reactive towards acid groups. Examples thereof include: methylenebisacrylamide, acrylates and methacrylates of polyols, such as butanediol diacrylate, hexanediol dimethacrylate, polyethylene glycol diacrylate, and trimethylolpropane triacrylate, and/or the acrylates and methacrylates of the oxalkylated mentioned polyols, such as of oxalkylated trimethylolpropane and oxalkylated pentaerythritol. Cross-linking agents of this type are known under the trade names Sartomer and Craynor (Crayvalley Kunstharze GmbH, 47918 Tönisvorst, Germany), of which Sartomer 415, Sartomer 454, Sartomer 494, Sartomer 610, and Craynor 435 are particularly usable; moreover, diesters and polyesters of polyols and oxethylated polyols with unsaturated monocarboxylic acids and/or polycarboxylic acids, such as (meth)acrylic acid esters of 1,2-propylene glycol, pentaerythritol, glycerol and polyglycerol, as well as monoesters of unsaturated alcohols and ethoxylated, unsaturated alcohols with unsaturated monocarboxylic acids and/or monocarboxylic acids, such as allyl acrylate and methacrylate, monoallyl maleate, allyl polyethylene glycol ether acrylate and methacrylate, allyl itaconate, allyl polyethylene glycol ether itaconate, and monoallyl polyethylene glycol ether maleate; additionally diallyl acrylamide, diallyl phthalate, diallyl adipate, triallyl citrate, and trimonoallyl polyethylene glycol ether citrate; moreover, allyl ethers of diols and polyols and their oxethylates, such as diallyl ethers of ethylene glycol, diethylene glycol, polyethylene glycol, triallyl ethers of glycerol, oxethylated glycerol, trimethylolpropane and oxethylated trimethylolpropane, tetraallylethers of pentaerythritol and oxethylated pentaerythritol, as well as tetraallyloxyethane, and polyglycidyl ether, for example, ethylene glycol diglycide ether and glycerol glycidyl ether. Additionally, amines and/or their salts and amides with at least two ethylenically unsaturated alkyl groups, such as di and triallylamine and tetraallylammonium chloride.

The usual initiators are used to initiate the radical polymerization, for example, peroxo and azo compounds, preferably water-soluble and/or dissociating peroxo and azo compounds, such as tert.-butyl hydroperoxide and 2,2'-azobis(2-methylpropionamidine) dihydrochloride; as well as redox systems formed of sodium and potassium peroxomonosulfate, sodium and potassium peroxodisulfate, and hydrogen peroxide with sodium and potassium sulfite, sodium and potassium formamidine sulfinate, and ascorbic acid.

When the redox systems are used, the oxidant is preferably prepared first and the reducing agent is added afterwards. Particularly in case of continuous polymerization, initiation is effected through photocatalysis with ultraviolet light and the known sensitizers.

The acid groups-containing monomers are preferably neutralized prior to the addition of the other components of the monomer solution, and preferably by preparing the base first. Suitable bases include alkali hydroxides, ammonia, and aliphatic, primary and secondary amines, as well as alkali carbonates and alkali hydrogen carbonates. The alkali hydroxides, sodium hydroxide and potassium hydroxide, as well as ammonia and soda are preferred.

Prior to polymerization, the monomer solution is cooled to a temperature ranging from 5–30° C., preferably 8–20° C. After initiation, polymerization takes place without inhibitory effects, i.e., without delay both with respect to the starting phase and in the further course of polymerization; this is a surprising fact and differs from the known methods.

Polymerization is carried out in the discontinuous batch method or, advantageously, in continuous manner, for example, on the belt reactor.

The formed polymer gel is then subjected to coarse grinding and comminution by means of conventional tearing and/or cutting tools. Comminution is preferably carried out by means of a cutting extruder via terminal breaker plates whose openings have a diameter ranging from 2–20 mm, preferably 5–15 mm, and most preferably 8–13 mm.

Subsequent neutralization of the comminuted polymer gel is carried out with the bases mentioned for partial neutralization, and again sodium hydroxide solution, potassium hydroxide solution and/or ammonia or soda, e.g., as $Na_2CO_3.10\ H_2O$ or as aqueous solution, are used. Neutralization is carried out in simple mixing units, for example, in a rotary drum or in a Drais-mixer, and the aqueous solution of the bases is introduced, for example, by means of nozzles or spray injectors. Neutralization is carried out until at least 50 mol-%, preferably 60–80 mol-%, of the acid groups-containing, polymerized monomer units are present as salts. The subsequent neutralization may also b e effected during comminution of the gel, for example, during size reduction in the extruder.

Owing to the slight partial neutralization of the monomer lye, the polymer gel's affinity to the base, preferably alkali lye, is improved to such an extent that a simple mixing unit is generally sufficient to carry out the further neutralization within a short period of time; thus mechanical damage of the polymer gel is prevented to a large extent.

The polymer gel is dried to a water content in the range of 5–20%-wt., preferably of $\leq 10\%$-wt., at temperatures in the range of 100–190° C. Subsequently, the dry product is ground into a polymer powder of a particle size in the range of 20–3,000 $\mu$m, preferably 150–850 $\mu$m. Subsequent cross-linkage of the polymer takes place on the surface of the dry polymer particles using at least one bi- or multifunctional cross-linker re acting with acid groups, preferably carboxyl groups, which is preferably applied in the form of a hydrous solution. Suitable secondary cross-linking agents include polyols, such as ethylene glycol, 1,2-propylene glycol, 1,4-butanediol, glycerol, di- and polyglycerol, pentaerythritol, the oxethylates of these polyols, as well as their esters with carboxylic acid or carbonic acid. Advantageously, an esterification catalyst, e.g., p-toluenesulfonic acid or phosphoric acid is added.

Further suitable cross-linkers include di- and polyglycidyl ethers of polyols and polyethylene glycols. Such compounds are commercially available under the trade name Denacol (Nagase (Europe) GmbH, Düsseldorf). Subsequent cross-linkage is carried out at temperatures ranging from 150–250° C., preferably 150–200° C., in a mixing unit, for example, a Nara-mixer.

The production method according to the present invention provides polymers standing out for considerably improved properties as compared to the conventional products. They have a retention in 0.9% aqueous NaCl-solution of at least 25 g/g polymer, preferably of 30 g/g, most preferably at least 33 g/g polymer. Under a pressure load of 50 g/cm$^2$, they achieve a liquid absorption of at least 25 g/g polymer, preferably at least 27 g/g polymer. The polymers according to the present invention, which are swollen by the absorption of water or aqueous liquids, have a high permeability for these liquids in swollen condition, even under pressure. Therefore, good distribution of the liquids is achieved, making full use of the absorption capacity of the polymers, when liquids turn up successively and repeatedly. Additionally, only very small amounts of the absorbed aqueous liquid are released again so that the rewet value amounts to a maximum of 2.0 g, preferably a maximum of 1.0 g. Their capability of absorbing liquids is further characterized by a very high swelling pressure of at least 700 g, preferably at least 850 g, more preferably of 900 g, and most preferably at least 1,000 g, according to the method of Stevens LFRA Texture Analyser. The polymers according to the present invention have a content of soluble polymer portions of below 10%-wt., preferably below 5%-wt., and most preferably below 3.5%-wt.

The absorbents obtained according to the process according to the present invention may be mixed with further substances. These substances include, for example, fillers, such as chalk, bentonite, or diatomaceous earth, as well as fibrous materials, such as hemp, viscose, or cellulose fibers. Color pigments, ultraviolet absorbents, antioxidants, and agricultural chemicals, such as fertilizers, herbicides, fungicides, and insecticides may also be used as components. The polymers according to the present invention may be used in many fields, preferably in hygiene products, such as diapers, sanitary napkins, wound patches, and incontinence bags, which serve the rapid and complete absorption of urine, menstrual blood, and exudation of wounds. In diapers the polymers are present at a weight percentage, relative to the weight amount of polymer and fluff, of 15–100%-wt., preferably 35–100%-wt, and most preferably of 30–70%-wt. In addition they may be used as component in packaging inserts to absorb liquids released from food, in cable filler materials to prevent ingress of water into seawater cables, as a component in current-conducting and light-transmitting cables, and in horticultural and agricultural substrates which are used as soil conditioners, or as depot materials for the controlled release of active substances, or as a component in artificial soils for plant cultivation. The present invention will be demonstrated in the examples that follow wherein the following test methods are used:

Retention (TB)

200 mg superabsorber is weighed into a tea bag and immersed into physiological saline (0.9%-wt. NaCl) for 30 min. After that, the tea bag is hung up at its corners for 10 min. to remove the free water and then centrifuged in a centrifuge at about 1,400 rpm. The blank reading and the initial weight are deducted from the resulting weight, and the result is converted to 1 g (TB g/g).

Absorption under pressure (AAP)

0.9 g superabsorber is evenly distributed in a cylinder having an inner diameter of 6 cm, its bottom consists of a sieve fabric having a mesh size of 35 $\mu$m. A weight of 20 g/cm$^3$ ($AAP_{0.3\ psi}$) or 50 g/cm$^3$ ($AAP_{0.7\ psi}$) presses on the superabsorber. The cylinder unit is weighed and then placed on a ceramic filter plate which immerses to the same level into physiological saline. After 1 hour, the cylinder unit is reweighed. The quotient from the weight difference of the cylinder units and the initial weight of the superabsorber is taken as absorption value $[(W_{after}-W_{before})/\text{initial weight}]$.

Rewet

The rewet test is carried out according to the instructions in EP 0 631 768 A1, p. 19, l. 39 to p. 20, l. 4; however, a 0.9% aqueous NaCl-solution is used instead of the synthetic urine.

Swelling Pressure (SP)

Determination of the swelling pressure SP is carried out by means of the Stevens L.F.R.A. Texture Analyser, C. Stevens & Son Ltd., Laboratory Division, St. Albans AL1 1 Ex Hertfordshire, England. 0.500 g superabsorber of size fraction 20–50 mesh is weighed into the measuring cylinder having a diameter of 2.7 cm, and 10 ml of 0.9% NaCl-solution is added. Then, the measuring cylinder is brought up by means of a lifting stage until the distance between the lower edge of the cylindrical measuring instrument and the surface of the sample in the measuring cylinder amounts to 12 mm. Through expansion of the gel the measuring cylinder is pressed upwards against a two-way load-sensing cell, and the load is indicated at the device in grams.

Residual Monomer (RM)

Determination of the residual amounts of acrylic acid in the superabsorber is carried out by gas chromatography, after extraction with physiological saline up to equilibrium state.

Soluble Contents (SC)

The polymer portion in a superabsorber that can be extracted within 16 hours and is related to carboxylic acid is determined according a method described in EP pat. application 0 205 674, pp. 34–37; however, physiological saline solution is used instead of the synthetic urine. The quantities are given in % by weight, relative to the dry, ground polymer.

The present invention will be illustrated in greater detail by means of the following examples and comparative data:

EXAMPLE 1

80 g acrylic acid and 0.24 g of a triacrylate of an oxethylated (15 moles of ethylene oxide) trimethylolpropane are dissolved in 244 g water and preneutralized with 4.4 g 50% sodium hydroxide solution. After ice cooling to 6 to 8° C. and purging with nitrogen to a maximum residual oxygen content of 0.3 ppm, 0.033 g 2,2'-azobis(2-methylpropionamidine) dihydrochloride, 0.12 g sodium persulfate, and 0.023 g hydrogen peroxide (35%) are introduced. Then, polymerization is started with 0.003 ascorbic acid. After an initiation phase of about 5 min., the temperature rises constantly and reaches the maximum temperature of 72° C. after about 20 min. Another 15 min. are maintained for secondary reaction, and then the resultant polymer gel is passed through a meat grinder. The comminuted mass is then mixed with 57.8 g 50% sodium hydroxide solution (increase of the neutralization degree to 70%) in a drum having a horizontal agitator shaft, dried to a water content of <10% at 140 to 160° C., and ground to a particle size of >180 to <850 µm. The obtained granulate is superficially re-cross-linked at 190° C. using ethylene carbonate (0.5% abs. dry, dissolved in water/acetone).

EXAMPLE 2

80 g acrylic acid and 0.2 g of a triacrylate of an oxethylated (3 moles of ethylene oxide) trimethylolpropane are dissolved in 244 g water and preneutralized with 8.9 g 50% sodium hydroxide solution. After ice cooling to 6 to 8° C. and purging with nitrogen to a maximum residual oxygen content of 0.3 ppm, 0.033 g 2,2'-azobis(2-methylpropionamidine) dihydrochloride, 0.12 g sodium persulfate, and 0.023 g hydrogen peroxide (35%) are introduced. Polymerization is started with 0.003 ascorbic acid. After about 20 min., the maximum temperature of 74° C. is achieved. For secondary reaction, another 15 min. are maintained, and then the resultant polymer gel is passed through a meat grinder. The comminuted mass is then mixed with 53.3 g 50% sodium hydroxide solution (increase of the neutralization degree to 70%) in a drum having a horizontal agitator shaft, dried to a water content of <10% at 140 to 160° C., and ground to a particle size of >180 to <850 µm. The obtained granulate is superficially re-cross-linked at 190° C. using ethylene carbonate (0.5% abs. dry, dissolved in water/acetone).

EXAMPLE 3

80 g acrylic acid and 0.16 g trimethylolpropane are dissolved in 244 g water and preneutralized with 8.9 g 50% sodium hydroxide solution. After ice cooling to 6 to 8° C. and purging with nitrogen to a maximum residual oxygen content of 0.3 ppm, 0.033 g 2,2'-azobis(2-methylpropionamidine) dihydrochloride, 0.12 g sodium persulfate, and 0.023 g hydrogen peroxide (35%) are introduced. Polymerization is then started with 0.003 ascorbic acid. After about 20 min., the maximum temperature of 74° C. is achieved. Another 15 min. are maintained for secondary reaction, and then the resultant polymer gel is passed through a meat grinder. The comminuted mass is then mixed with 53.3 g 50% sodium hydroxide solution (increase of the neutralization degree to 70%) in a drum having a horizontal agitator shaft, dried to a water content of <10% at 140 to 160° C., and ground to a particle size of >180 to <850 µm. The obtained granulate is superficially re-cross-linked at 190° C. using ethylene carbonate (0.5% abs. dry, dissolved in water/acetone).

EXAMPLE 4

80 g acrylic acid and 0.24 g of a triacrylate of an oxethylated (15 moles of ethylene oxide) trimethylolpropane are dissolved in 244 g water and preneutralized with 8.9 g 50% sodium hydroxide solution. After ice cooling to 6 to 8° C. and purging with nitrogen to a maximum residual oxygen content of 0.3 ppm, 0.033 g 2,2'-azobis(2-methylpropionamidine) dihydrochloride, 0.12 g sodium persulfate, and 0.023 g hydrogen peroxide (35%) are introduced. Polymerization is started with 0.003 ascorbic acid. After about 20 min., the maximum temperature of 74° C. is achieved. Another 15 min. are maintained for secondary reaction, and then the resultant polymer gel is passed through a meat grinder. The comminuted mass is then mixed with 53.3 g 50% sodium hydroxide solution (increase of the neutralization degree to 70%) in a drum having a horizontal agitator shaft, dried to a water content of <10% at 140 to 160° C., and ground to a particle size of >180 to <850 µm. The obtained granulate is superficially re-cross-linked at 190° C. using ethylene carbonate (0.5% abs. dry, dissolved in water/acetone).

EXAMPLE 5

80 g acrylic acid and 1 g polyethylene(600)-glycol diacrylate are dissolved in 240 g water together with 1 g Mowiol 5/88 (Hoechst) and preneutralized with 8.9 g 50% sodium hydroxide solution. After ice cooling to 6 to 8° C. and purging with nitrogen to a maximum residual oxygen content of 0.3 ppm, 0.23 g 2,2'-azobis(2-methylpropionamidine) dihydrochloride and 0.24 g hydrogen peroxide (35%) are introduced. Then, polymerization is started with 0.02 g ascorbic acid.

After about 15 min., the maximum temperature of 75° C. is achieved. After a 15 min.-downtime for secondary reaction, the resultant polymer gel is passed through a meat grinder. The comminuted mass is then mixed with 190.7 g uncalcined, solid soda (increase of the neutralization degree to 70%) in a drum having a horizontal agitator shaft, dried to a water content of <10% at 140 to 160° C., and ground to a particle size of >180 to <850 µm. The obtained granulate is superficially re-cross-linked at 190° C. using ethylene carbonate (0.5% abs. dry, dissolved in water/acetone).

EXAMPLE 6

80 g acrylic acid and 1 g polyethylene(400)-glycol diacrylate are dissolved in 240 g water together with 1 g Mowiol 5/88 (Hoechst) and preneutralized with 26.7 g 50% sodium hydroxide solution. After ice cooling to 6 to 8° C. and purging with nitrogen to a maximum residual oxygen content of 0.3 ppm, 0.23 g 2,2'-azobis(2-methylpropionamidine) dihydrochloride and 0.24 g hydrogen peroxide (35%) are introduced. Then, polymerization is started with 0.02 g ascorbic acid. After about 1 5 min., the maximum temperature of 75° C. is achieved. After a 20 min.-downtime for secondary reaction, further processing was carried out as described in Example 1; for subsequent neutralization, 35.5 g 50% sodium hydroxide solution was used.

EXAMPLE 7

80 g acrylic acid and 1 g polyethylene(400)-glycol diacrylate are dissolved in 240 g water together with 1 g Mowiol 5/88 (Hoechst) and preneutralized with 4.5 g 50% sodium hydroxide solution. After ice cooling to 6 to 8° C. and purging with nitrogen to a maximum residual oxygen content of 0.3 ppm, 0.23 g 2,2'-azobis(2-methylpropionamidine) dihydrochloride and 0.24 g hydrogen peroxide (35%) are introduced. Then, polymerization is started with 0.02 g ascorbic acid. After about 25 min., the maximum temperature of 72° C. is achieved. After a 20 min.-downtime for secondary reaction, further processing was carried out as described in Example 1; for subsequent neutralization, 39.9 g 50% sodium hydroxide solution was used.

Comparative Example 1
Polymerization Trial without Preneutralization Degree 80 g acrylic acid and 0.24 g of a triacrylate of an oxethylated (3 moles of ethylene oxide) trimethylolpropane were dissolved in 244 g water. After ice cooling to 6 to 8° C. and purging with nitrogen to a maximum residual oxygen content of 0.3 ppm, 0.033 g 2,2'-azobis(2-methylpropionamidine) dihydrochloride, 0.12 g sodium persulfate, and 0.023 g hydrogen peroxide (35%) were introduced. Then, it was attempted to start the polymerization (as in Example 1) with 0.003 g ascorbic acid. This failed, and 0.02 g ascorbic acid were additionally added. After a downtime of about 5 min., polymerization started and the maximum temperature of 64° C. was achieved after about 30 min. For secondary reaction, another 15 min. were maintained, and then the resultant polymer gel was passed through a meat grinder. The comminuted mass was then mixed with 62.2 g sodium hydroxide solution (increase of the neutralization degree to 70%) in a drum having a horizontal agitator shaft, dried to a water content of <10% at 140 to 160° C., and ground to a particle size of >180 to <850 μm. The obtained granulate was superficially re-cross-linked at 190° C. using ethylene carbonate (0.5% abs. dry, dissolved in water/acetone).

TABLE 1

Properties of the polymers

| | TB (g/g) | $AAP_{0.3}$ (g/g) | $AAP_{0.7}$ (g/g) | SP 20/120 min. (g) | SC %-wt. | Rewet (g) |
|---|---|---|---|---|---|---|
| Example 1 | 34 | 36 | 28 | 850/900 | 4.5 | 0.5 |
| Example 2 | 35 | 36 | 29 | 880/920 | 5 | 1.0 |
| Example 3 | 35 | 36 | 28 | 850/890 | 5 | 1.0 |
| Example 4 | 35 | 36 | 29 | 860/920 | 5 | 1.0 |
| Example 5 | 34 | 37 | 30 | 1040/940 | 4 | 0.2 |
| Example 6 | 34 | 37 | 30 | 1120/925 | 5 | 1.0 |
| Example 7 | 35 | 36 | 29 | 910/920 | 4 | 2.0 |
| Comp. Ex. 1 | 32 | 34 | 25 | 820/850 | 4 | 2.5 |
| Sanwet IM 4000* | 31 | 29 | 19 | 577/496 | 5.2 | 2.5 |
| Sanwet IM 7000* | 35 | 29.5 | 16 | 609/522 | 5.4 | 2.9 |
| Sanwet IM 7000* | 33 | 34 | 20 | 529/567 | 2.8 | 8.5 |

*by Hoechst AG

TABLE 2

Retentions of acidic polymer gels (about 24% active substance, related to acrylic acid, according to Example 2 or Comparative Example 1) with differing neutralization degree:

| Example | Neutralization degree (%) | TB (g/g) |
|---|---|---|
| Comp. Ex. 1 | 0 | 2.04 |
| 2 | 5 | 2.25 |
| 2 | 10 | 2.80 |
| 2 | 20 | 4.96 |
| 2 | 30 | 8.90 |

The data in Table 2 show the extreme increase in the absorption capacity of acrylate gels for aqueous liquids in the neutralization range of 0 to 30% of the acrylic-acid-polymer gels, on the basis of the retention values of physiological saline.

What is claimed is:
1. A moisture absorbing article comprising a powdery, cross-linked polymer, comprising:
   a) 55–99.9%-wt. of at least one unsaturated, polymerizable, acid group-containing monomer which is present as a salt neutralized to the extent of 5–30 mol-%,
   b) 0–40%-wt. of at least one unsaturated monomer which is copolymerizable with the monomer according to a),
   c) 0.01–5.0%-wt. of at least one cross-linking agent, and
   d) 0–30%-wt. of at least one water-soluble polymer,
   with the sum of components a)–d) amounting to 100%-wt., and the portion of the polymerized acid group-containing monomer a) in the polymer is neutralized to the extent of at least 50 mol-%, and the polymer is additionally cross-linked on the surface and it has
   a retention for a 0.9% aqueous NaCl-solution of at least 25 g/g polymer,
   a liquid absorption under a pressure of 50 g/cm² of at least 25 g/g polymer,
   a swelling pressure after 20 minutes of at least 700 g, relative to 1 g of polymer,
   a maximum soluble content of 3.5–10%-wt. after 16 hours, and
   a maximum rewet of 2.0 g, wherein said article is selected from the group consisting of a sanitary article, a current-conducting cable, and a light-transmitting cable.

2. The moisture absorbing articles of claim 1, wherein said sanitary article is selected from the group consisting of a diaper, a sanitary napkin, and an incontinence article.

3. The moisture absorbing article of claim 1, further comprising fluff.

4. The moisture absorbing article of claim 3, wherein the weight percentage of said cross-linked polymer is 15–70-wt.% of the amount of said cross-linked polymer and fluff.

5. The moisture absorbing article of claim 4, wherein the weight percentage of said cross-linked polymer is 30–70-wt.% of the amount of said cross-linked polymer and fluff.

6. The moisture absorbing article of claim 3, wherein said article is a diaper.

7. The moisture absorbing article of claim 4, wherein said article is a diaper.

\* \* \* \* \*